(12) United States Patent
Sagedahl et al.

(10) Patent No.: US 8,333,003 B2
(45) Date of Patent: Dec. 18, 2012

(54) BIFURCATION STENT CRIMPING SYSTEMS AND METHODS

(75) Inventors: Mark Sagedahl, Alexandria, MN (US);
Adam Jennings, Buffalo, MN (US);
Robert Lucas, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 963 days.

(21) Appl. No.: 12/123,000

(22) Filed: May 19, 2008

(65) Prior Publication Data

US 2009/0287289 A1    Nov. 19, 2009

(51) Int. Cl.
*A61M 29/00* (2006.01)

(52) U.S. Cl. ............... 29/516; 29/505; 29/506; 29/508; 72/402

(58) Field of Classification Search ........... 29/446, 29/448, 469.5, 505, 506, 508, 516, 513; 72/402
See application file for complete search history.

(56) References Cited

U.S. PATENT DOCUMENTS

| | | |
|---|---|---|
| 3,792,603 A | 2/1974 | Orain |
| 4,448,195 A | 5/1984 | LeVeen et al. |
| 4,461,163 A | 7/1984 | Kralowetz |
| 4,484,585 A | 11/1984 | Baier |
| 4,578,982 A | 4/1986 | Schrock |
| 4,601,701 A | 7/1986 | Mueller, Jr. |
| 4,769,005 A | 9/1988 | Ginsburg et al. |
| 4,776,337 A | 10/1988 | Palmaz |
| 4,913,141 A | 4/1990 | Hillstead |
| 4,994,071 A | 2/1991 | MacGregor |
| 4,998,923 A | 3/1991 | Samson et al. |
| 5,019,085 A | 5/1991 | Hillstead |
| 5,092,152 A | 3/1992 | Miller et al. |
| 5,122,154 A | 6/1992 | Rhodes |
| 5,195,984 A | 3/1993 | Schatz |
| 5,219,355 A | 6/1993 | Parodi et al. |
| 5,261,263 A | 11/1993 | Whitesell |
| 5,316,023 A | 5/1994 | Palmaz et al. |
| 5,397,305 A | 3/1995 | Kawula et al. |
| 5,449,353 A | 9/1995 | Watanabe et al. |

(Continued)

FOREIGN PATENT DOCUMENTS

DE    29701758    3/1997

(Continued)

OTHER PUBLICATIONS

Foley et al., "Bifurcation Lesion Stenting," The Thoraxcentre Journal, vol. 8, No. 4, 5 pages, 1996.

(Continued)

*Primary Examiner* — Jermie Cozart
*Assistant Examiner* — Christopher Besler
(74) *Attorney, Agent, or Firm* — Seager, Tufte & Wickhem, LLC (57) ABSTRACT

A stent crimping system and method for use in preparing a bifurcation catheter assembly for use in a patient. The catheter assembly includes main and side catheter branches and a stent. The stent includes a side branch aperture through which the side catheter branch extends. The stent is crimped onto the main and side catheter branches with a crimping mechanism in two crimping steps. In the first crimping step, only a distal end portion of the stent is crimped while the side catheter branch remains extending through the side branch opening of the stent and remains positioned outside of the crimping mechanism. In a second crimping step, the entire stent is crimped with the crimping mechanism.

16 Claims, 7 Drawing Sheets

U.S. PATENT DOCUMENTS

| | | | |
|---|---|---|---|
| 5,477,856 A | 12/1995 | Lundquist |
| 5,571,086 A | 11/1996 | Kaplan et al. |
| 5,609,627 A | 3/1997 | Goicoechea et al. |
| 5,632,763 A | 5/1997 | Glastra |
| 5,643,278 A | 7/1997 | Wijay |
| 5,644,945 A | 7/1997 | Baldwin et al. |
| 5,672,169 A | 9/1997 | Verbeek |
| 5,681,345 A | 10/1997 | Euteneuer |
| 5,683,345 A | 11/1997 | Waksman et al. |
| 5,697,971 A | 12/1997 | Fischell et al. |
| 5,725,519 A | 3/1998 | Penner et al. |
| 5,749,825 A | 5/1998 | Fischell et al. |
| 5,755,734 A | 5/1998 | Richter et al. |
| 5,755,735 A | 5/1998 | Richter et al. |
| 5,755,778 A | 5/1998 | Kleshinski |
| 5,772,669 A | 6/1998 | Vrba |
| 5,776,142 A | 7/1998 | Gunderson |
| 5,788,707 A | 8/1998 | Del Toro et al. |
| 5,797,952 A | 8/1998 | Klein |
| 5,824,055 A | 10/1998 | Spiridigliozzi et al. |
| 5,833,694 A | 11/1998 | Poncet |
| 5,873,906 A | 2/1999 | Lau et al. |
| 5,876,374 A | 3/1999 | Alba et al. |
| 5,893,868 A | 4/1999 | Hanson et al. |
| 5,906,640 A | 5/1999 | Penn et al. |
| 5,906,759 A | 5/1999 | Richter |
| 5,908,405 A | 6/1999 | Imran et al. |
| 5,921,995 A | 7/1999 | Kleshinski |
| 5,935,161 A | 8/1999 | Robinson et al. |
| 5,941,908 A | 8/1999 | Goldsteen et al. |
| 5,944,727 A | 8/1999 | Ahari et al. |
| 5,951,569 A | 9/1999 | Tuckey et al. |
| 5,957,929 A | 9/1999 | Brenneman |
| 5,957,941 A | 9/1999 | Ream |
| 5,961,546 A | 10/1999 | Robinson et al. |
| 5,961,548 A | 10/1999 | Shmulewitz |
| 5,968,052 A | 10/1999 | Sullivan, III et al. |
| 6,013,092 A | 1/2000 | Dehdashtian et al. |
| 6,017,362 A | 1/2000 | Lau |
| 6,027,460 A | 2/2000 | Shturman |
| 6,033,434 A | 3/2000 | Borghi |
| 6,048,361 A | 4/2000 | Von Oepen |
| 6,056,722 A | 5/2000 | Jayaraman |
| 6,056,775 A | 5/2000 | Borghi et al. |
| 6,059,813 A | 5/2000 | Vrba et al. |
| 6,066,155 A | 5/2000 | Amann et al. |
| 6,071,286 A | 6/2000 | Mawad |
| 6,077,297 A | 6/2000 | Robinson et al. |
| 6,082,990 A | 7/2000 | Jackson et al. |
| 6,090,127 A | 7/2000 | Globerman |
| 6,096,045 A | 8/2000 | Del Toro et al. |
| 6,096,073 A | 8/2000 | Webster et al. |
| 6,099,497 A | 8/2000 | Adams et al. |
| 6,110,191 A | 8/2000 | Dehdashtian et al. |
| 6,117,156 A | 9/2000 | Richter et al. |
| 6,120,522 A | 9/2000 | Vrba et al. |
| 6,132,450 A | 10/2000 | Hanson et al. |
| 6,143,014 A | 11/2000 | Dehdashtian et al. |
| 6,146,415 A | 11/2000 | Fitz |
| 6,152,944 A | 11/2000 | Holman et al. |
| 6,165,195 A | 12/2000 | Wilson et al. |
| 6,165,210 A | 12/2000 | Lau et al. |
| 6,176,116 B1 | 1/2001 | Wilhelm et al. |
| 6,178,802 B1 | 1/2001 | Reynolds |
| 6,187,015 B1 | 2/2001 | Brenneman |
| 6,190,360 B1 | 2/2001 | Iancea et al. |
| 6,190,393 B1 | 2/2001 | Bevier et al. |
| 6,210,380 B1 | 4/2001 | Mauch |
| 6,210,429 B1 | 4/2001 | Vardi et al. |
| 6,210,431 B1 | 4/2001 | Power |
| 6,214,036 B1 | 4/2001 | Letendre et al. |
| 6,221,090 B1 | 4/2001 | Wilson |
| 6,221,097 B1 | 4/2001 | Wang et al. |
| 6,224,587 B1 | 5/2001 | Gibson |
| 6,238,410 B1 | 5/2001 | Vrba et al. |
| 6,246,914 B1 | 6/2001 | de la Rama et al. |
| 6,254,593 B1 | 7/2001 | Wilson |
| 6,258,052 B1 | 7/2001 | Milo |
| 6,258,073 B1 | 7/2001 | Mauch |
| 6,264,688 B1 | 7/2001 | Herklotz et al. |
| 6,280,466 B1 | 8/2001 | Kugler et al. |
| 6,287,277 B1 | 9/2001 | Yan |
| 6,287,330 B1 | 9/2001 | Johansson et al. |
| 6,290,673 B1 | 9/2001 | Shanley |
| 6,299,636 B1 | 10/2001 | Schmitt et al. |
| 6,302,906 B1 | 10/2001 | Goicoechea et al. |
| 6,319,275 B1 | 11/2001 | Lashinski et al. |
| 6,322,548 B1 | 11/2001 | Payne et al. |
| 6,325,826 B1 | 12/2001 | Vardi et al. |
| 6,331,186 B1 | 12/2001 | Wang et al. |
| 6,342,066 B1 | 1/2002 | Toro et al. |
| 6,350,277 B1 | 2/2002 | Kocur |
| 6,360,577 B2 | 3/2002 | Austin |
| 6,361,544 B1 | 3/2002 | Wilson et al. |
| 6,361,555 B1 | 3/2002 | Wilson |
| 6,364,893 B1 | 4/2002 | Sahatjian et al. |
| 6,371,978 B1 | 4/2002 | Wilson |
| 6,375,660 B1 | 4/2002 | Fischell et al. |
| 6,379,372 B1 | 4/2002 | Dehdashtian et al. |
| 6,387,117 B1 | 5/2002 | Arnold, Jr. et al. |
| 6,387,120 B2 | 5/2002 | Wilson et al. |
| 6,391,050 B1 | 5/2002 | Broome |
| 6,406,487 B2 | 6/2002 | Brenneman |
| 6,406,489 B1 | 6/2002 | Richter et al. |
| 6,416,529 B1 | 7/2002 | Holman et al. |
| 6,436,104 B2 | 8/2002 | Hojeibane |
| 6,443,880 B2 | 9/2002 | Blais et al. |
| 6,443,980 B1 | 9/2002 | Wang et al. |
| 6,475,166 B1 | 11/2002 | Escano |
| 6,478,814 B2 | 11/2002 | Wang et al. |
| 6,482,211 B1 | 11/2002 | Choi |
| 6,488,694 B1 | 12/2002 | Lau et al. |
| 6,508,835 B1 | 1/2003 | Shaolian et al. |
| 6,510,722 B1 | 1/2003 | Ching et al. |
| 6,514,261 B1 | 2/2003 | Randall et al. |
| 6,514,281 B1 | 2/2003 | Blaeser et al. |
| 6,517,558 B2 | 2/2003 | Gittings et al. |
| 6,520,983 B1 | 2/2003 | Colgan et al. |
| 6,520,988 B1 | 2/2003 | Colombo et al. |
| 6,530,947 B1 | 3/2003 | Euteneuer et al. |
| 6,533,805 B1 | 3/2003 | Jervis |
| 6,540,719 B2 | 4/2003 | Bigus et al. |
| 6,544,278 B1 | 4/2003 | Vrba et al. |
| 6,554,841 B1 | 4/2003 | Yang |
| 6,568,235 B1 | 5/2003 | Kokish |
| 6,582,459 B1 | 6/2003 | Lau et al. |
| 6,589,262 B1 | 7/2003 | Honebrink et al. |
| 6,596,020 B2 | 7/2003 | Vardi et al. |
| 6,599,315 B2 | 7/2003 | Wilson |
| 6,602,226 B1 | 8/2003 | Smith et al. |
| 6,607,506 B2 | 8/2003 | Kletschka |
| 6,607,552 B1 | 8/2003 | Hanson |
| 6,613,067 B1 | 9/2003 | Johnson |
| 6,623,518 B2 | 9/2003 | Thompson et al. |
| 6,629,350 B2 | 10/2003 | Motsenbocker |
| 6,629,981 B2 | 10/2003 | Bui et al. |
| 6,651,478 B1 | 11/2003 | Kokish |
| 6,660,030 B2 | 12/2003 | Shaolian et al. |
| 6,669,718 B2 | 12/2003 | Besselink |
| 6,692,483 B2 | 2/2004 | Vardi et al. |
| 6,695,862 B2 | 2/2004 | Cox et al. |
| 6,699,275 B1 | 3/2004 | Knudson et al. |
| 6,739,033 B2 | 5/2004 | Hijlkema et al. |
| 6,925,847 B2 | 8/2005 | Motsenbocker |
| 7,225,518 B2 | 6/2007 | Eidenschink et al. |
| 7,314,480 B2 | 1/2008 | Eidenschink et al. |
| 7,367,989 B2 | 5/2008 | Eidenschink |
| 2001/0001890 A1 | 5/2001 | Austin |
| 2001/0049548 A1 | 12/2001 | Vardi et al. |
| 2002/0019664 A1 | 2/2002 | Douglas |
| 2002/0019665 A1 | 2/2002 | Dehdashtian et al. |
| 2002/0022874 A1 | 2/2002 | Wilson |
| 2002/0038140 A1 | 3/2002 | Yang et al. |
| 2002/0038141 A1 | 3/2002 | Yang et al. |
| 2002/0072755 A1 | 6/2002 | Bigus et al. |
| 2002/0111675 A1 | 8/2002 | Wilson |
| 2002/0116045 A1 | 8/2002 | Eidenschink |

| | | |
|---|---|---|
| 2002/0120320 A1 | 8/2002 | Wang et al. |
| 2002/0138966 A1 | 10/2002 | Motsenbocker |
| 2003/0023298 A1 | 1/2003 | Jervis |
| 2003/0055483 A1 | 3/2003 | Gumm |
| 2003/0055484 A1 | 3/2003 | Lau et al. |
| 2003/0144671 A1 | 7/2003 | Brooks et al. |
| 2003/0181923 A1 | 9/2003 | Vardi |
| 2003/0192164 A1 | 10/2003 | Austin |
| 2003/0195546 A1 | 10/2003 | Solar et al. |
| 2004/0138737 A1 | 7/2004 | Davidson et al. |
| 2004/0199239 A1 | 10/2004 | Austin et al. |
| 2004/0260379 A1 | 12/2004 | Jagger et al. |
| 2004/0267352 A1 | 12/2004 | Davidson et al. |
| 2005/0149161 A1 | 7/2005 | Eidenschink et al. |
| 2005/0154442 A1 | 7/2005 | Eidenschink et al. |
| 2005/0154450 A1 | 7/2005 | Larson et al. |
| 2005/0182473 A1 | 8/2005 | Eidenschink et al. |
| 2005/0183259 A1 | 8/2005 | Eidenschink et al. |
| 2005/0273149 A1 | 12/2005 | Tran et al. |
| 2006/0036315 A1 | 2/2006 | Yadin et al. |
| 2006/0100694 A1 | 5/2006 | Globerman |
| 2008/0086191 A1* | 4/2008 | Valencia et al. ............. 623/1.11 |

FOREIGN PATENT DOCUMENTS

| | | |
|---|---|---|
| FR | 2678508 | 1/1993 |
| WO | 0121076 | 3/2001 |
| WO | 0121103 | 3/2001 |
| WO | 0211646 | 2/2002 |
| WO | 03017872 | 3/2003 |
| WO | 03055414 | 7/2003 |
| WO | 03061529 | 7/2003 |

OTHER PUBLICATIONS

Oda et al., "Fork Stenting for Bifurcation Lesions," Journal of Interventional Cardiology, vol. 9, No. 6, pp. 445-454, Dec. 1996.

Pomerantz et al., "Distortion of Palmaz-Schatz Stent Geometry Following Side-Branch Balloon Dilation through the Stent in a Rabbit Model," Catheterization and Cardiovascular Diagnosis, vol. 40, pp. 422-426, 1997.

Schampaert et al., "The V-Stent: A Novel Technique for Coronary Bifurcation Stenting," Catheterization and Cardiovascular Diagnosis, vol. 39, No. 3, pp. 320-326, 1996.

* cited by examiner

BIFURCATION STENT CRIMPING SYSTEMS AND METHODS

TECHNICAL FIELD

This disclosure relates to catheter assemblies configured for treatment of a vessel bifurcation.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure relates to stent crimping systems and methods for use in preparing a bifurcation catheter assembly for use in a patient. One aspect of the present disclosure relates to a catheter assembly that includes main and side catheter branches and a stent. The stent includes a side branch aperture through which the side catheter branch extends. The stent is crimped onto the main and side catheter branches with a crimping mechanism in two crimping steps. In the first crimping step, only a distal end portion of the stent is crimped while the side catheter branch remains extending through the side branch opening of the stent and remains positioned outside of the crimping mechanism. In a second crimping step, the entire stent is crimped with the crimping mechanism.

Another aspect of the present disclosure relates to a recess feature defined in the crimping mechanism. The crimping mechanism includes a plurality of radially moveable crimping members that define a crimping chamber and a side surface. A recess can be defined in the side surface. The recess can be sized to receive a distal end portion of the side catheter branch during the first crimping step.

There is no requirement that an arrangement include all features characterized herein to obtain some advantage according to this disclosure.

DETAILED DESCRIPTION

This disclosure relates to bifurcation treatment systems, catheter assemblies, methods of assembling such bifurcation treatment systems and assemblies, and related devices and apparatuses for use in such methods. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems.

The systems, apparatuses and methods disclosed herein can be used to assemble all or portions of various bifurcation treatment systems and assemblies. One example step in the assembly of a bifurcation treatment system includes crimping a stent onto a pair of catheter branches—a main catheter branch and a side catheter branch. The main catheter branch includes a main balloon, a side balloon configured to extend radially outward relative to the main balloon when inflated, and a main guidewire housing. The side catheter branch defines a branch guidewire housing and is arranged to extend through a side branch opening of the stent. The side branch opening of the stent is defined in a sidewall of the stent at a location between distal and proximal open ends of the stent. In some assembly systems and methods, three or more applications of a crimping force to the stent via a crimping assembly is required to properly crimp the stent without causing damage to the main and branch vessels.

In one arrangement, the side catheter branch must be removed from the stent prior to initial crimping of a distal portion of the stent onto the main catheter branch. In a second crimping step, the side catheter branch is inserted through the side branch opening of the stent and then only the proximal portion of the stent is crimped onto the main and side catheter branches. In a third crimping step, the entire stent is crimped onto the main and side catheter branches to help reduce a profile of the stent particularly in the area of the side branch opening.

The use of three or more separate crimping steps adds significant time and complexity to the process of assembling and crimping a bifurcation catheter assembly. Further, a crimping process that includes removal of the side catheter branch from the stent during or between any one of the crimping steps typically requires that the side catheter branch is disconnected from the main catheter branch. This reduces the possibility of certain bonding arrangements for connection of the side catheter branch to the main catheter branch at a location proximal of the stent. Such a proximal bond is desirable in some dual monorail (e.g., dual rapid exchange (Rx)) catheter systems and bifurcation catheter assemblies. Bond arrangements possible post-crimping of the stent are usually limited to adhesive bonds. Bonding arrangements requiring application of heat (e.g., heat bonding and laser bonding) sometimes cannot be used in close proximity to a stent. Bonding the side catheter branch to the main catheter branch after crimping the stent can also inhibit opportunities to conduct positive pressure testing of the main and side catheter branches, since application of a positive pressure to the catheter assembly after the stent is crimped thereto tends to re-expand the stent.

The Example Apparatuses and Assembly Methods of FIGS. 1-9

Figure 1:
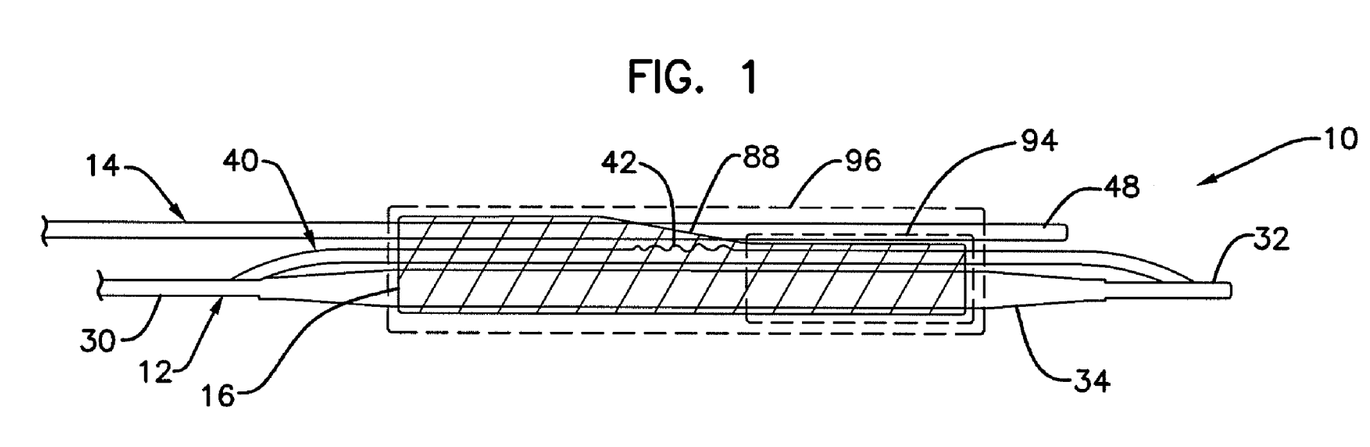
FIG. 1 is a schematic side view of an example catheter assembly in accordance with principles of the present disclosure with the entire stent in a crimped state.

Referring now to FIG. 1, an example catheter assembly 10 is shown and described. The catheter assembly 10 includes a main catheter branch 12, a side catheter branch 14, and a stent 16. The stent 16 is mounted to the main and side catheter branches 12, 14 with the side catheter branch 14 extending through a side branch opening 88 of the stent 16. The stent 16 is shown crimped to the main and side catheter branches 12, 14. Crimping of the stent 16 is performed in two steps as will be described in further detail below. In a first step, a crimping force is applied to a distal portion of the stent in the area labeled 94 distal of the side branch opening 88. In a second step, a crimping force is applied to the entire stent 16 in the crimping area labeled 96. No additional application of crimping forces (i.e., crimping steps) should be required prior to, in between, or after application of the crimping force is to the first and second crimping areas 94, 96 in order for the catheter assembly 10 to be prepared for application in a patient.

Figure 2:
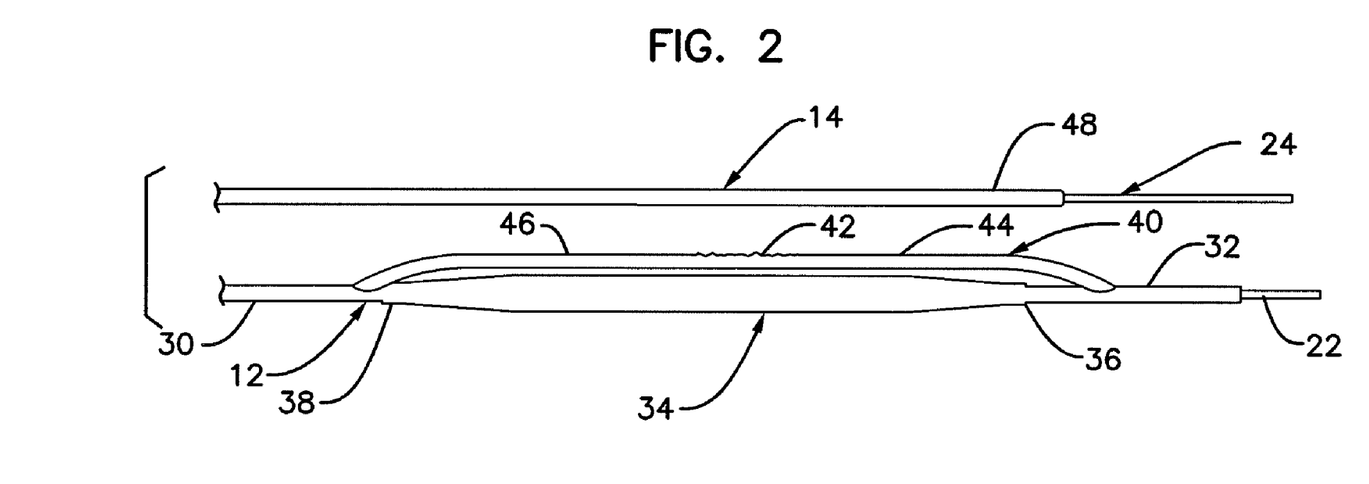
FIG. 2 is a schematic side view of main and side catheter branches of the catheter assembly shown in FIG. 1 with mandrels inserted therein.
Figure 15:
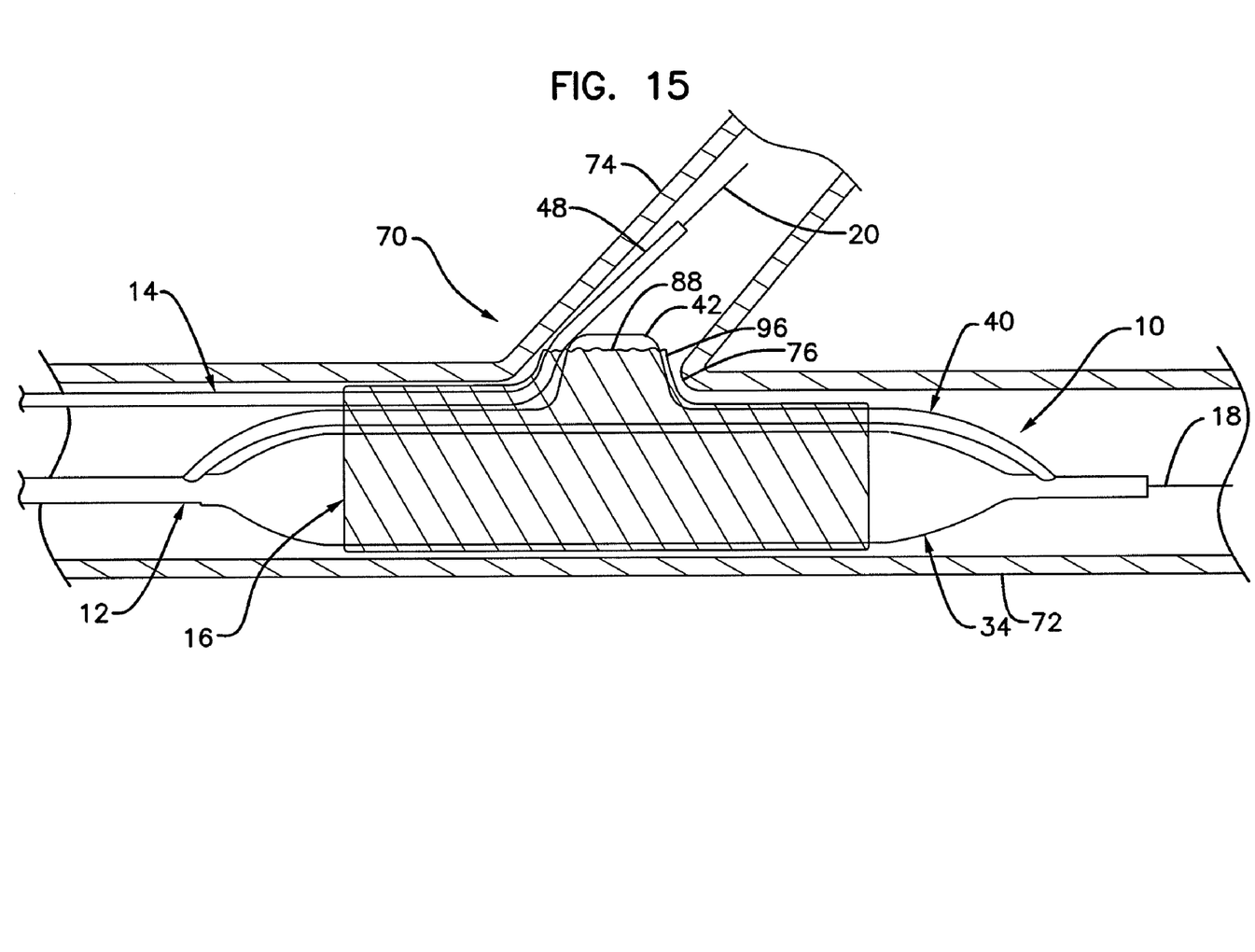
FIG. 15 is a schematic side view of the catheter assembly shown in FIG. 1 with the main and side balloons in an inflated state to expand the stent into engagement with a vessel bifurcation.

The process or method of assembling the catheter assembly 10 and crimping stent 16 into the package shown in FIG. 1 begins with first advancing first and second mandrels 22, 24 into the main and side catheter branches 12, 14, respectively as shown in FIG. 2. The main catheter branch 12 can include a catheter shaft 30, a main guidewire housing 32, a main balloon 34, and a side balloon arrangement 40. The main balloon 34 includes a distal end portion 36 and a proximal end portion 38. The side balloon arrangement 40 includes a side balloon 42 (shown in a deflated state in FIGS. 1 and 2 and in an inflated state in FIG. 15), a distal inflation segment 44, and proximal inflation segment 46. Typically, the side balloon 42 is connected in fluid communication with the main balloon 34 via at least one of the distal and proximal inflation segments 44, 46. The side balloon 42 is configured to extend radially outward from the main balloon 34 upon inflation of the side balloon 42 as shown in FIG. 15.

The side catheter branch 14 can be connected to the main catheter branch 12 at a location proximal of the main balloon 34 and typically within a range of about 10 to about 100 mm from the main balloon 34 to facilitate a dual monorail catheter system arrangement. Providing such a proximal bond between the main and side catheter branches 12, 14 permits positive pressure testing of the catheter assembly 10 prior to crimping the stent 16. Vacuum pressure testing of the catheter assembly 10 can be conducted after formation of the proximal bond and prior to or after the crimping step.

Typically, the first and second mandrels 22, 24 are extended from distal ends of the main guidewire housing 32 and the side catheter branch 14 a distance in the range of about 5 to about 40 mm, and more preferably in the range of about 20 to about 30 mm. The main guidewire housing 32 typically extends through an interior of the main balloon 34 and into the catheter shaft 30. A space defined between the main guidewire housing 32 and an interior of the catheter shaft 30 can define an inflation lumen that provides delivery of inflation fluid to the main and side balloons 34, 42, and deflation thereof. The main guidewire housing 32 and the side catheter branch 14 define main and branch guidewire lumens sized to receive main and branch guidewires 18, 19 (see FIG. 15).

Figure 3:
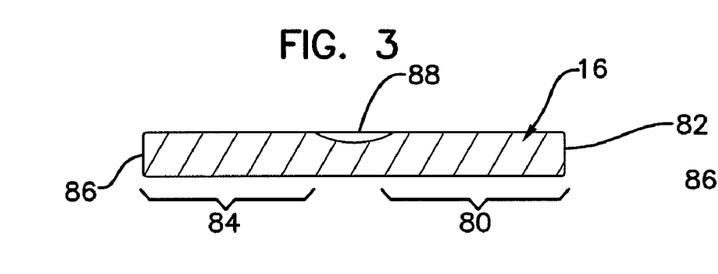
FIG. 3 is a schematic side view of an example stent in accordance with principles of the present disclosure.

FIG. 3 illustrates the stent 16 in a pre-flared, pre-crimped state. The stent 16 includes a distal end portion 80, a distal open end 82, a proximal end portion 84, a proximal open end 86, a side branch opening 88, and a plurality of side expandable members 90 (see FIG. 15). The proximal and distal end portions 80, 84 are typically defined in a region between the side branch opening 88 and the distal and proximal open ends 82, 86, respectively. In some arrangements, the side branch opening 88 and at least portions of the side expandable members 90 that help define the side branch opening 88 are not included in either of the distal and proximal end portions 80, 84.

There are many stent constructions possible for stent 16. Some example stent constructions are disclosed in U.S. Published Patent Application Nos. 2004/0267352 and 2006/0036315, which are incorporated herein by reference in their entirety.

Figure 4:
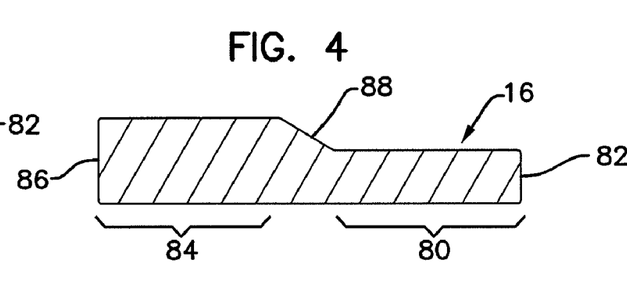
FIG. 4 is a schematic side view of the example stent shown in FIG. 3 in a flared state.
Figure 5:
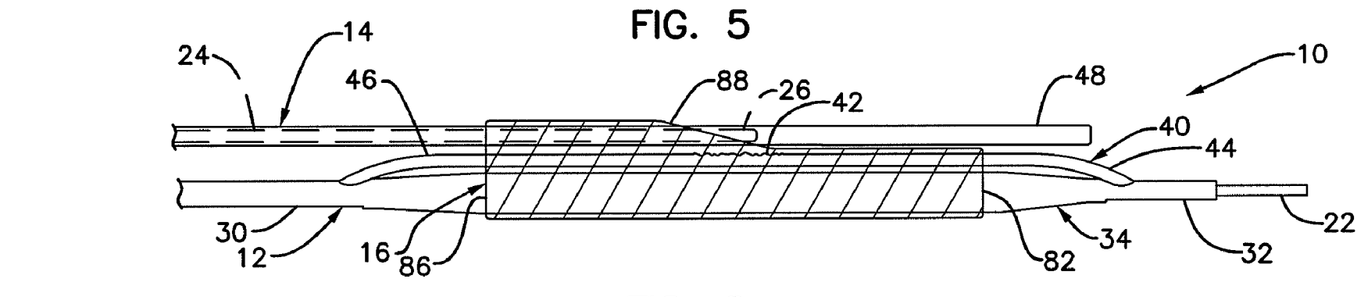
FIG. 5 is a schematic side view of the catheter assembly shown in FIG. 1 with the mandrel of the side catheter branch retracted proximal of a side branch opening of the stent.

FIG. 4 illustrates stent 16 in a flared state. Portions of the stent 16 can be flared to a larger internal diameter for improved ease in inserting the main and side catheter branches 12, 14 into the stent 16. A flaring tool can be inserted into one or both of the distal and proximal open ends 82, 86 to expand the stent 16. The flaring tool can have different shapes and sizes to provide the desired amount of flaring or expansion of the stent in certain regions of the stent. FIG. 4 illustrates the proximal end portion 84 flared or expanded to a greater size than the distal end portion 80. The increased size of the proximal end portion 84 can provide space necessary for positioning both the main and side catheter branches 12, 14 in the proximal end portion 84, while the distal end portion 80 is sized to receive only the main catheter branch 12 as shown in FIG. 5.

With the main and side catheter branches 12, 14 positioned within the stent 16 with the side catheter branch 14 extending out of the side branch opening 88, the second mandrel 24 is retracted proximally until a distal end 26 thereof is positioned in alignment with the side branch opening 88. Positioning of the mandrel 24 in this orientation permits bending or other radial or lateral movement of the side catheter branch distal end 48 relative to the main catheter branch 12 and stent 16. Movement of the distal end 48 while maintaining the remaining portions of the side catheter branch 14 fixed relative to the main catheter branch 12 can help in interfacing with a crimping mechanism 50 to provide crimping of the distal end portion 80 of the stent 16.

Figure 6:
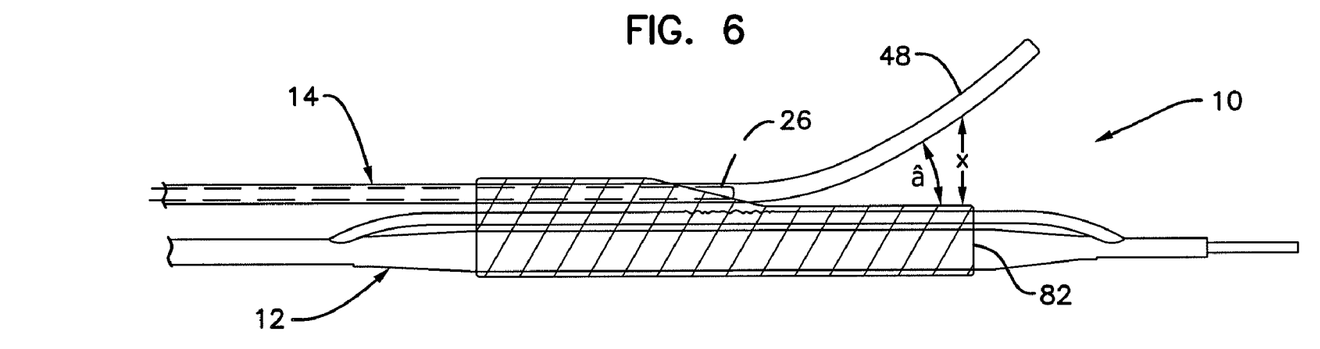
FIG. 6 is a schematic side view of the catheter assembly shown in FIG. 5 with a distal end of the side catheter branch moved radially away from the main catheter branch.

FIG. 6 illustrates the distal end portion 48 of the side catheter branch 14 moved radially outward relative to the distal open end 82 of the stent 16 a distance X and at an angle β. The distance X can be in the range of, for example, 5 to about 20 mm. The distance X can vary depending on, for example, the size and shape of the stent 16 and the materials and construction of the side catheter branch 14. The angle β can be in the range of about 10 to about 45 degrees, and more preferably in the range of about 25 to about 35 degrees. The spaced arrangement of the distal end 48 relative to the distal open end 82 of the stent 16 is preferably maintained without any external force. Such a bent or curved shape as shown in FIG. 6 can be at least temporarily set in the side catheter branch 14 by over extending the distal end 48 a distance in the direction of angle β, for example, a distance X in the range of 10 to 40 mm or an angle β of 45 to 90 degrees and maintain that position for a predetermined time period.

Figures 7, 8:
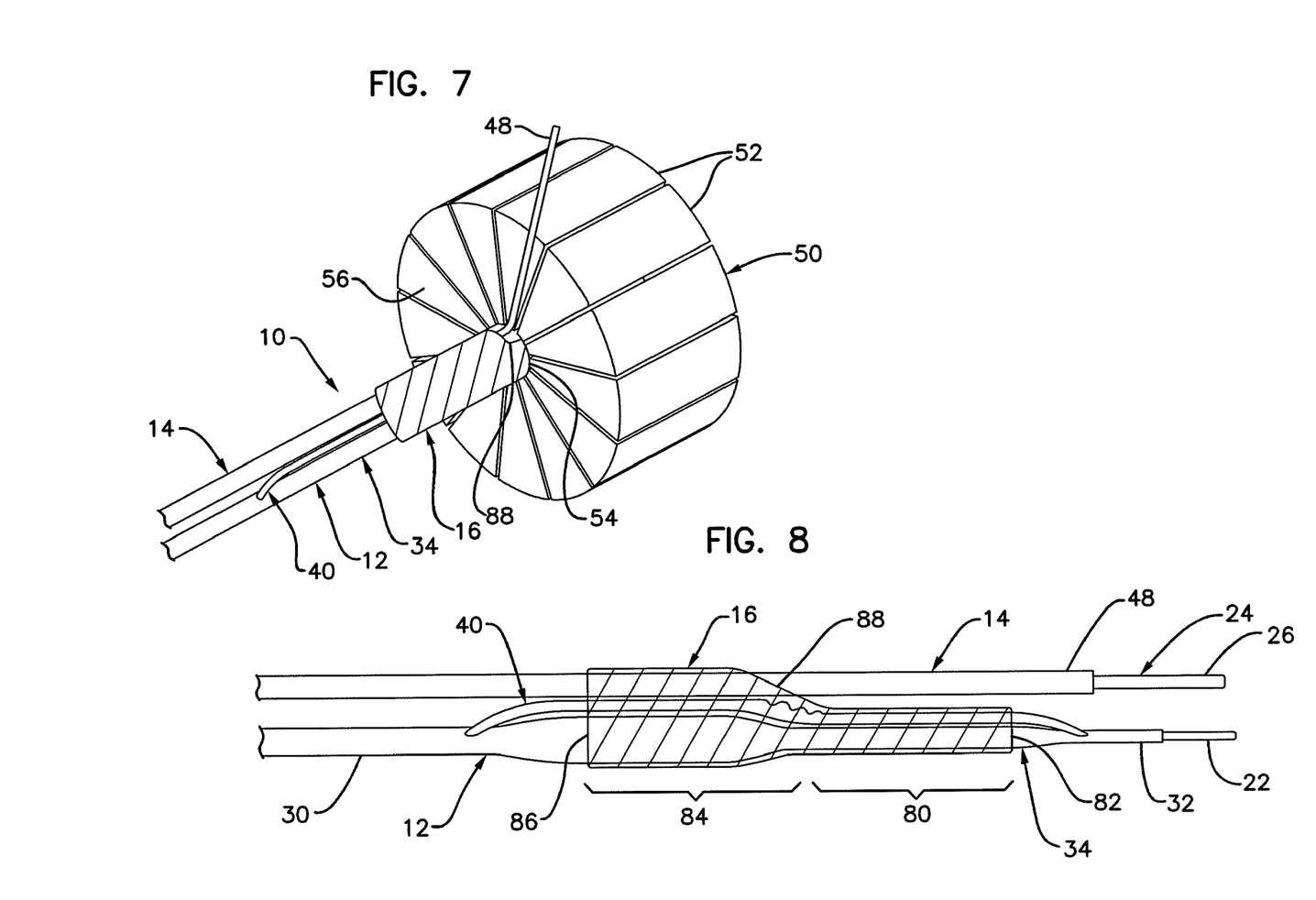
FIG. 7 is a schematic perspective view of the catheter assembly shown in FIG. 6 with a distal end portion of the stent positioned in a crimping mechanism.
FIG. 8 is a schematic side view of the catheter assembly shown in FIG. 6 with the distal end portion of the stent in a crimped state.

The catheter assembly 10 with the bent distal end 48 of the side catheter branch 14 is then inserted into a crimping mechanism 50 as shown in FIG. 7. The crimping mechanism 50 includes a plurality of crimping blades 52 and a front face 56. The crimping blades 52 are arranged adjacent to each other to define a core 54 sized to receive the catheter assembly 10. The of crimping blades 52 are moved radially inward and outward to change the size of core 54 and to apply a radially inward directed crimping force upon the stent 16.

A distal end of the catheter assembly 10 is inserted distally into the core 54 up to the point of the side branch opening 88 of the stent 16. The distal end portion 80 of the stent 16 along with the distal end portion 36 of the main balloon 34 and the distal inflation segment 44 of the side balloon arrangement 44 and distal portions of the main guidewire housing 32 are all positioned within the core 54. The pre-bent shape of the side catheter branch 14 as shown in FIG. 6 can maintain the side catheter branch 14 out of the core 54 when positioning the catheter assembly in the orientation shown in FIG. 7. The side catheter branch 14 maintains a position extending through the proximal end portion 84 of the stent and protrudes out of the side branch opening 88. The distal end 48 of the side catheter branch 14 remains out of the core 54 and is bent radially away from the stent 16 along the front face 56 of the crimping mechanism 50. In the arrangement shown at FIG. 7, the distal end portion 48 of the side catheter branch 14 extends at an angle β of about 90 degrees relative to the stent 16 and a longitudinal axis of the main catheter branch 12.

With the catheter assembly 10 arranged as shown in FIG. 7, a crimping force is applied to the distal end portion 80 of the stent 16 with the crimping mechanism 50 to reduce an outer profile (i.e., draw down) the distal end portion of the stent 16. Typically, the amount of time required to arrange the catheter assembly 10 as shown in FIG. 7 and apply the crimping force with the crimping mechanism 50, followed by removal of the catheter assembly 10 is in the range of about 20 to about 60 seconds. Arranging the distal end portion 48 of the side catheter branch 14 in the bent arrangement shown in FIG. 7 for this relatively short period of time typically does not result in permanent deformation of or damage to the side catheter branch 14 in the area of the side branch opening 88 of stent 16. After removal of the catheter assembly 10 from the crimping mechanism 50, the second mandrel 24 is advanced distally out of the distal end portion 48 until the distal end 26 is extending distally beyond a side catheter branch 14 a distance of, for example, about 20 to about 30 mm. The second mandrel 24 has a generally linear shape and a stiffness sufficient to realign the side catheter branch 14 in a linear arrangement as shown in FIG. 8.

FIG. 8 further illustrates how the distal end portion 80 of the stent 16 has been drawn down to an outer profile size reduced from the arrangement shown in FIG. 5 and significantly smaller than the outer profile of the proximal end portion 84 of the stent 16. The catheter assembly 10 in the arrangement shown in FIG. 8 is now prepared for a second crimping step. The catheter assembly 10 shown in FIG. 8 is advanced into the core 54 of the crimping mechanism 50 so that the entire stent is positioned within the core 54 (i.e., the compression area 96 shown in FIG. 1). The first and second mandrels 22, 24 prevent damage to the first and second catheter branches 12, 14 during application of the crimping force by the crimping mechanism 50. When the crimping force is applied by the crimping mechanism 50, the proximal end portion 84 as well as any intervening portions of stent 16 between the proximal and distal end portions 80, 84 in the area of side branch opening 88 are compressed or otherwise drawn down to a minimum outer profile (i.e., the size shown in FIG. 1). The crimping force is then released from the crimping mechanism, the core size 54 is increased, and the catheter assembly 10 with fully crimped stent 16 is removed from the crimping mechanism 50.

Figures 9, 10:
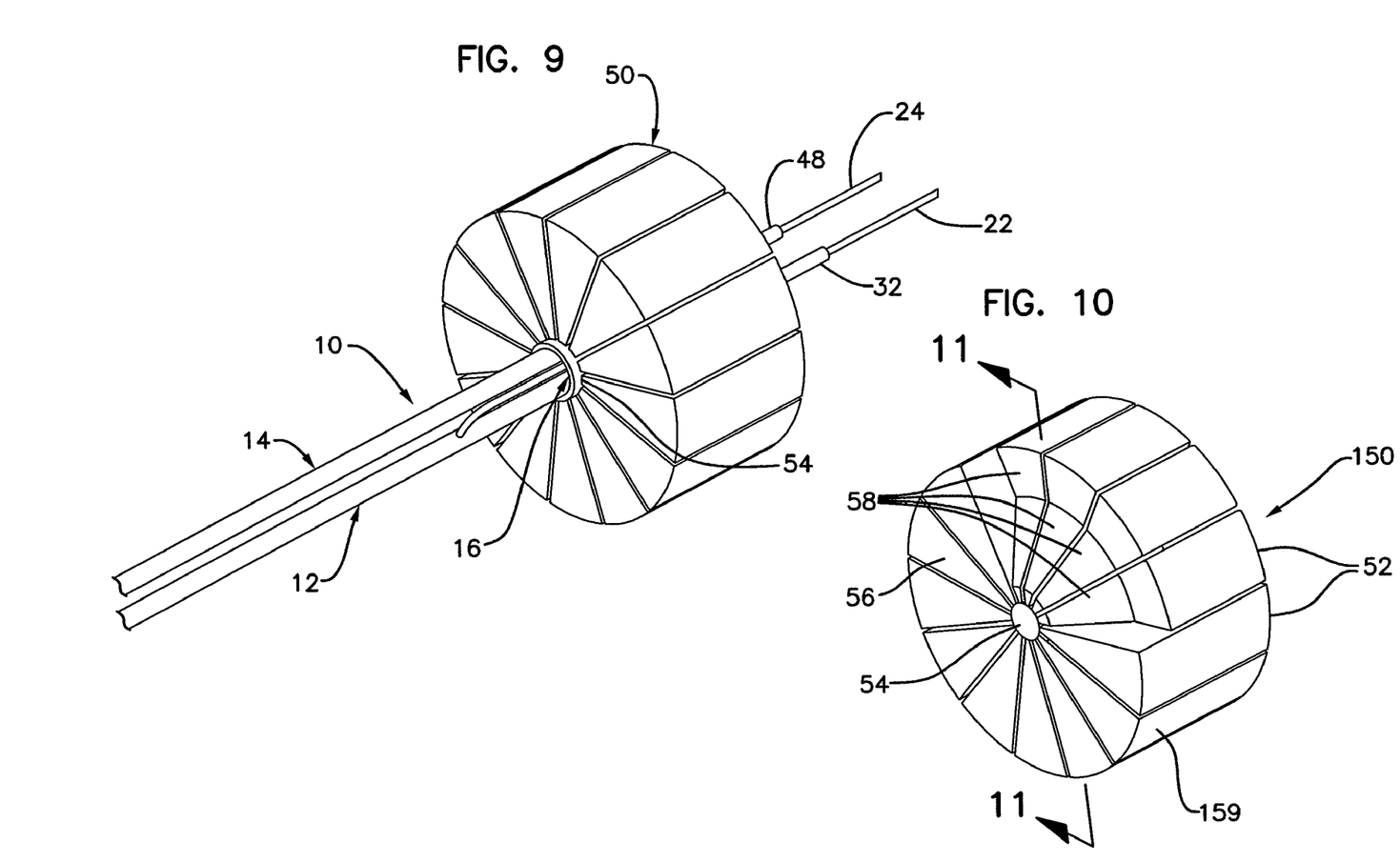
FIG. 9 is a schematic perspective view of the catheter assembly shown in FIG. 8 with the entire stent positioned within the crimping mechanism.
FIG. 10 is a schematic perspective view of another example crimping mechanism in accordance with principles of the present disclosure.

Typically, the amount of force applied by the crimping mechanism 50 during the crimping steps shown and described with reference to FIGS. 7 and 9 is in the range of about 10 to about 15 psi, and more typically in the range of about 12 to about 14 psi.

In further steps of preparing the catheter assembly 10 for application in a patient can include removing the first and second mandrels 22, 24 from the catheter assembly 10 and replacing mandrels 22, 24 with product application mandrels (not shown). A further step can include applying a balloon protecting sleeve over portions of the catheter assembly 10, particularly in the area of the main and side balloons 34, 42. The catheter assembly 10 can also be positioned within a guiding catheter prior to use in a patient.

FIG. 15 illustrates use of the catheter assembly 10 with the stent 16 crimped as shown in FIG. 1 for treatment of a vessel bifurcation 70. The vessel bifurcation 70 includes a main vessel 72, a branch vessel 74, and an ostium or opening into the branch vessel 76. Steps of treating the vessel bifurcation 70 with the catheter assembly 10 can include first advancing main and branch guidewires 18, 20 into the main and branch vessels 72, 74, respectively. Distal ends of the main and branch guidewires 18, 20 are inserted into the distal end of main guidewire housing 32 and the distal end 48 of side catheter branch 14, respectively. The catheter assembly 10 is then advanced over the guidewires 18, 20 to the vessel bifurcation 70. The catheter assembly 10 is adjusted axially and radially until the side branch opening 88 of the stent 16 is aligned with the ostium 76. Positioning of the distal end portion 48 of the side catheter branch 14 within the branch vessel 74 can improve attaining and maintaining alignment of the side branch opening 88 with the ostium 76.

With the catheter assembly 10 properly aligned relative to the vessel bifurcation 70, the main balloon 34 is inflated to expand the stent into engagement with the main vessel 72, and the side balloon 42 is inflated to expand the expandable members 90 of the stent 16 through the ostium 76 and into at least partial engagement with the branch vessel 74. The balloons 34, 42 are then deflated and the main and side catheter branches 12, 14 are retracted proximally from the stent 16. Further treatment of the vessel bifurcation 70 can be performed by advancing a post dilation balloon through the side branch opening 88 to inflate it and further expand the expandable members 90 into engagement with the branch vessel 74. In still further treatment steps, a secondary stent can be advanced through the side branch opening 88 and into the branch vessel 74. The secondary stent can be expanded into engagement with the branch vessel 74 and at least partially overlaps the expandable members 90.

Further Examples and Arrangements of FIGS. 10-14

Figure 11:
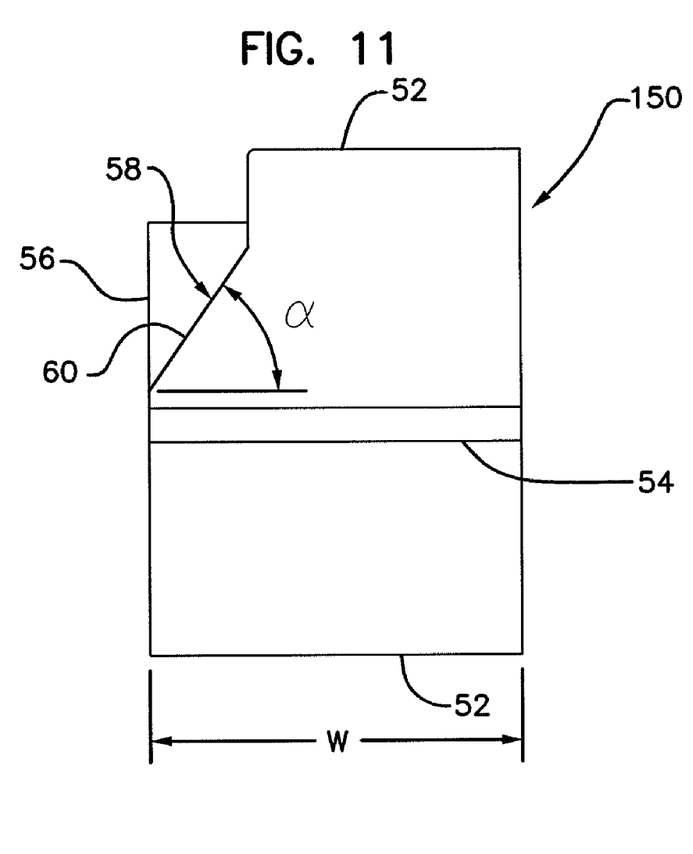
FIG. 11 is a schematic cross-sectional view of the crimping mechanism shown in FIG. 10 taken along cross-sectional indicators 11-11.

The crimping mechanism can have features that can help reduce the bent angle of the side catheter branch 14 during the first crimping step shown in FIG. 7. FIGS. 10 and 11 illustrate another example crimping mechanism 150 that includes a plurality of crimping blades 52, a core 54, a front face 56, and a recessed portion 58. Although alternatives are possible, the recess portion 58 can be formed by removing portions of at least one of the plurality of crimping blades 52 along the front face 56. Preferably, the crimping blades 52 have a full width W along the core 54 to ensure that an internal circumference core is defined along the width W. The recessed portion 58 can extend from the core 54 at the front face 56 inward into the crimping mechanism 50 as shown in FIG. 11. The recessed portion 58 can include a slanted or ramped surface 60 extending at an angle γ from a central axis of the core 54.

The recessed portion 58 provides a space within which the distal end portion 48 of the side catheter branch 14 can extend during the first crimping step shown in FIG. 7. The recessed portion 58 provides for a less significant bend in the side catheter branch 14 at the side branch opening 88, which can reduce potential incidence of damage, permanent deformation, or other adverse effects on the side catheter branch 14 during the first crimping step.

Figure 12:
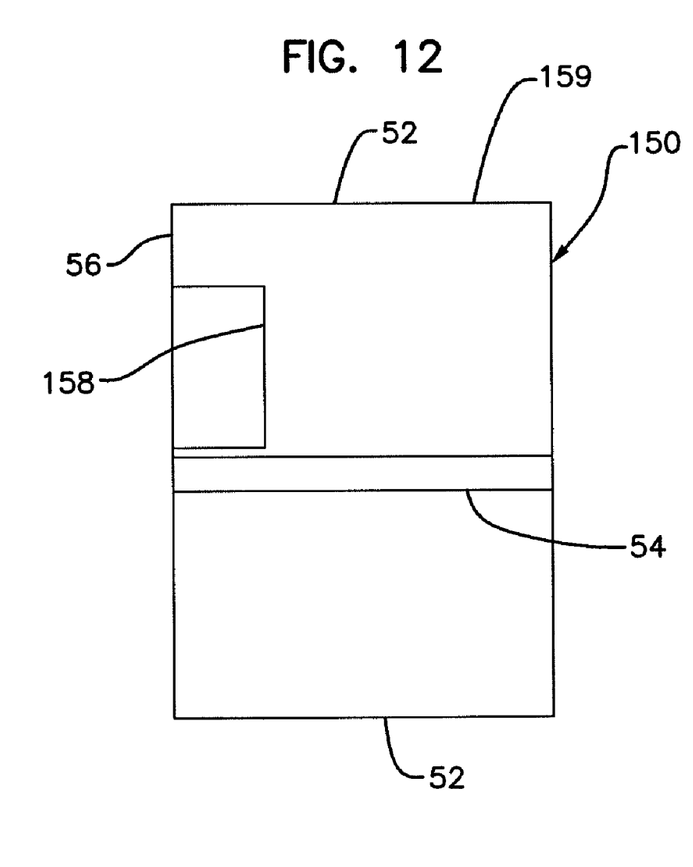
FIG. 12 is a schematic cross-sectional view of another example crimping mechanism in accordance with principles of the present disclosure.

FIG. 12 illustrates another example of recessed portion 158 constructed as a generally rectangular shape recess that does not extend to an outer periphery 159 of the crimping mechanism 150. Many other recess portion constructions are possible. In some arrangements, the recessed portion is defined in only a single one of the plurality of crimping blades 52. In other examples, each of a plurality of adjacent crimping blades has a different amount of material removed to define a recess portion 58 with a specific shape and size.

The recessed portions 58, 158 described herein are defined relative to a front face 56 that is arranged generally perpendicular to a longitudinal axis of the crimping mechanism 150. In other arrangements, the front face 56 its can be arranged at a non-perpendicular angle relative to the longitudinal axis of the crimping mechanism 150.

Other constructions for crimping mechanisms are described in U.S. Pat. No. 7,225,518, which discloses different core constructions and other features related to crimping mechanisms. U.S. Pat. No. 7,225,518 patent is incorporated herein by reference.

Figure 13:
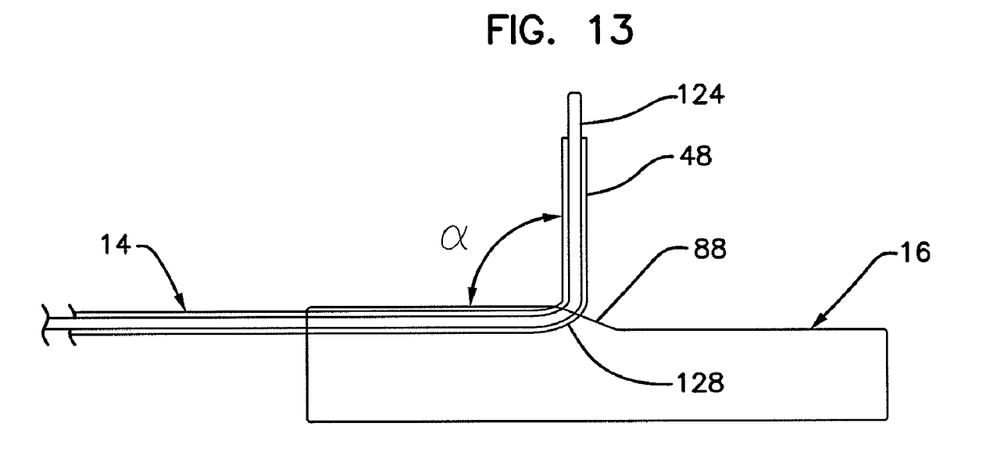
FIG. 13 is a schematic side view illustrating another example mandrel configuration in accordance with principles of the present disclosure.

FIG. 13 illustrates an alternative construction for a second mandrel 124. The second mandrel 124 includes a bend portion 128 that provides a bend angle α. The bend angle α preferably is in the range of about 45 to about 120 degrees, and more preferably in the range of about 80 to about 100 degrees. Providing a second mandrel 124 within the side catheter branch 14 with a bend portion 128 arranged at the side branch opening 88 of the stent 16 can reduce incidence of buckling, pinching, and other types of deformation in the side catheter branch 14 when arranging the catheter assembly 10 in the crimping mechanism 50 during the first crimping step shown in FIG. 7.

The mandrel 124 can be inserted into the side catheter branch 14, typically through the distal end portion 48 prior to or after positioning of the side catheter branch 14 within the stent 16 and extending through the side branch opening 88. The mandrel 124 can be removed from the side catheter branch 14 after the first crimping step and prior to insertion of the second mandrel 24 into the side catheter branch 14 (see FIG. 8) prior to the second crimping step (see FIG. 9).

The angle α can vary depending on, for example, the construction of the crimping mechanism 50. When the crimping mechanism includes a recess portion (see crimping mechanism 150 described with reference to FIGS. 10-12), the angle α can be greater than 90 degrees and up to an angle wherein the sum of angle α and angle γ is about 180 degrees.

In other arrangements, the second mandrel 124 can include more than one bend or angled portion 128. For example, one angled portion can be arranged at the side branch opening 88, while a second angled portion can be arranged distal of the side branch opening 88 along the length of the side catheter branch 14. The second angled portion can be positioned at, for example, a location that would provide improved positioning of the distal end portion 48 within the recessed portion 58 of the crimping mechanism 150.

Figure 14:
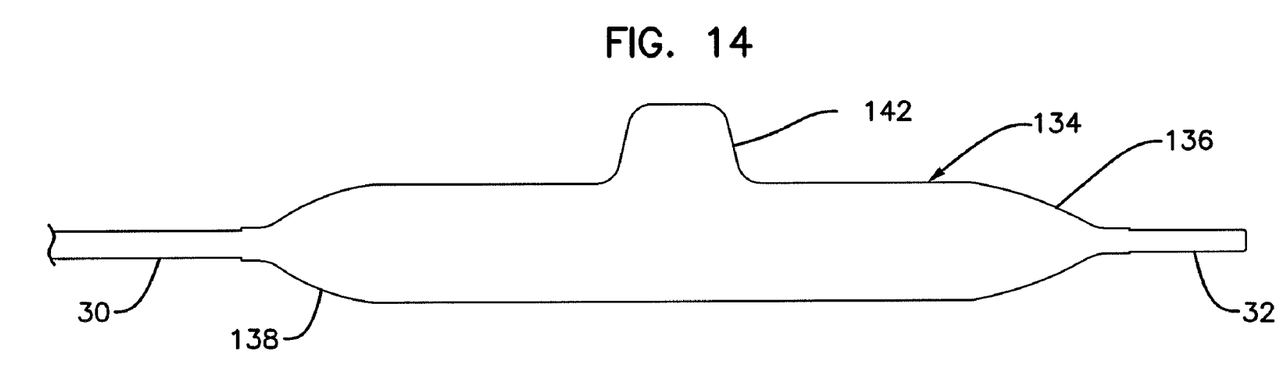
FIG. 14 is a schematic side view of another example main catheter branch having a side balloon formed integral with a main balloon thereof in accordance with principles of the present disclosure.

The example catheter assembly 10 described above with reference to FIGS. 1-9 includes a side balloon arrangement 40 with the side balloon 42 as a separate inflatable balloon structure from the main balloon 34. In other arrangements, the side balloon can be formed integral with or otherwise positioned on the main balloon. FIG. 14 illustrates a main balloon 134 with a side balloon 142 positioned on an external surface thereof at a location spaced between the distal and proximal ends 136, 138. The side balloon 142 can be formed integral with the main balloon 134. In other arrangements, the side balloon 142 can be formed as a separate piece that is mounted to the main balloon 134 and a separate assembly using, for example, a bonding arrangement such as adhesives or heat bonding.

Materials and Other Considerations

The example systems disclosed herein may be used in over-the-wire or rapid exchange systems. Some example rapid exchanges systems are disclosed in U.S. Published Patent Application No. 2003/0181923 to Vardi et al., which application is incorporated herein by reference.

The materials used in the balloons, catheter shafts, and guidewire housing members disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429 and 6,325,826 to Vardi et al., and co-pending U.S. patent application Ser. No. 10/644,550, filed on Aug. 21, 2003, and titled "Stent With a Protruding Branch Portion For Bifurcated Vessels," the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

CONCLUSION

One aspect of the present disclosure relates to a method of crimping a stent of a catheter assembly with a stent contracting assembly. The catheter assembly includes a main catheter branch, a side catheter branch, and a stent. The stent includes a proximal open end, a distal open end, and a side branch opening located between the proximal and distal open ends. The side catheter branch extends into the proximal open end of the stent and out of the side branch opening, and the main catheter branch extends into the proximal open end of the stent and out of the distal open end of the stent. The stent contracting assembly defines an outer profile reduction chamber and a side surface. One step of the method includes inserting the catheter assembly into the chamber until a distal portion of the stent up to a location distal of the side branch opening of the stent is positioned in the chamber, while the side catheter branch remains positioned outside of the chamber. The method also includes reducing an outer profile of the distal portion of the stent, inserting the entire stent into the chamber, and reducing an outer profile of a proximal portion of the stent.

Another aspect of the present disclosure relates to a stent contracting assembly. The assembly includes a plurality of moveable contracting members that define a stent crimping chamber that is constructed and arranged to receive at least a portion of a catheter assembly. The stent crimping chamber is configured to reduce an outer profile of a stent of the catheter assembly. The stent crimping chamber includes a longitudinal axis, and the plurality of moveable contracting members define a side surface of the stent contracting assembly. The side surface is arranged generally perpendicular to the longitudinal axis. A recess is defined in the side surface. The recess is sized to receive a portion of the catheter assembly when reducing an outer profile of a portion of the stent.

Another aspect of the present disclosure relates to a method of crimping a stent of a catheter assembly with a stent contracting assembly. The catheter assembly includes a main catheter branch, a side catheter branch, and a stent. The stent includes a proximal open end, a distal open end, and a side branch opening located between the proximal and distal open ends. The side catheter branch extends out of the side branch opening, and the main catheter branch extends through the stent from the proximal open end to the distal open end. The stent contracting assembly defines an outer profile reduction chamber. The method can include inserting portions of the catheter assembly into the chamber, and reducing an outer profile of the stent in only two activations of the stent contracting assembly to reduce a size of the chamber.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of crimping a stent of a catheter assembly with a stent contracting assembly, the catheter assembly including a main catheter branch, a side catheter branch, and a stent, the stent including a proximal open end, a distal open end, and a side branch opening located between the proximal and distal open ends, wherein the side catheter branch extends into the proximal open end of the stent and out of the side branch opening, and the main catheter branch extends into the proximal open end of the stent and out of the distal open end of the stent, the stent contracting assembly defining a outer profile reduction chamber and a side surface defining an opening into the chamber, the method comprising:
    (a) inserting the catheter assembly through the opening in the side surface into the chamber until a distal portion of the stent up to a location distal of the side branch opening of the stent is positioned in the chamber, moving a distal end of the side catheter branch radially outward relative to the main catheter branch such that the distal end of the side catheter branch is bent radially away from the stent and remains outside of the stent contracting assembly and adjacent the side surface;
    (b) reducing an outer profile of the distal portion of the stent;
    (c) realigning the side catheter branch with the main catheter branch and inserting the entire stent into the chamber; and
    (d) reducing an outer profile of a proximal portion of the stent.

2. The method of claim 1, wherein the step of inserting the entire stent into the chamber further includes inserting portions of side catheter branch into the chamber.

3. The method of claim 1, further comprising inserting a first mandrel into the main catheter branch prior to inserting the distal portion of the stent into the chamber.

4. The method of claim 3, further comprising inserting a second mandrel into the side catheter branch prior to inserting the entire stent into the chamber and after reducing an outer profile of the distal portion of the stent.

5. The method of claim 1, further comprising connecting the side catheter branch to the main catheter branch at a location proximal of the stent prior to the step of inserting the distal portion of the stent into the chamber.

6. The method of claim 1, wherein the main catheter branch includes a main balloon and a side balloon, the side balloon being configured to extend radially outward relative to the main balloon when inflated, the method further comprising aligning the side balloon with the side branch opening of the stent prior to the step of inserting the distal portion of the stent into the chamber.

7. The method of claim 1, wherein the step of inserting the distal portion of the stent into the chamber includes engaging the side catheter branch against the side surface.

8. The method of claim 1, further comprising inserting a pre-bent mandrel in the side catheter branch prior to the step of inserting the distal portion of the stent into the chamber, the pre-bent mandrel including a bend portion, wherein the bend portion being arranged in the side catheter branch adjacent the side branch opening of the stent.

9. The method of claim 1, wherein the stent outer profile is reduced to a state required for use of the catheter assembly to treat a vessel bifurcation.

10. The method of claim 1, wherein the side surface of the stent contracting assembly is arranged perpendicular to a longitudinal axis of the chamber, and the side surface includes a recess, the method further including maintaining a portion of the side catheter branch in the recess during the step of reducing an outer profile of the distal portion of the stent.

11. A method of crimping a stem of a catheter assembly with a stent contracting assembly, the catheter assembly including a main catheter branch, a side catheter branch, and a stent, the stent including a proximal open end, a distal open end, and a side branch opening located between the proximal and distal open ends, wherein the side catheter branch extends out of the side branch opening, and the main catheter branch extends through the stent from the proximal open end to the distal open end, the stent contracting assembly defining a outer profile reduction chamber, the method comprising:
    (a) inserting portions of the catheter assembly into the chamber while moving a distal end of the side catheter branch radially outward relative to the main catheter branch such that the distal end of the side catheter branch is bent radially away from the main catheter branch and remains outside the stent contracting assembly; and
    (b) reducing an outer profile of the stent in only two activations of the stent contracting assembly to reduce a size of the chamber.

12. The method of claim 11, wherein the step of inserting portions of the catheter assembly into the chamber includes inserting a distal portion of the stent into the chamber to a point distal of the side branch opening of the stent prior to a first activation of the stent contracting assembly.

13. The method of claim 12, wherein the step of inserting portions of the catheter assembly into the chamber includes inserting the entire stent into the chamber after the first activation of the stent contracting assembly and before a second activation of the stent contracting assembly.

14. The method of claim 12, further comprising maintaining the distal end of the side catheter branch outside of the chamber during the first activation of the stent contracting assembly.

15. The method of claim 14, further comprising positioning a portion of the side catheter branch within the chamber during a second activation of the stent contracting assembly.

16. The method of claim 11, further comprising inserting a mandrel into the main and side catheter branches.

* * * * *

UNITED STATES PATENT AND TRADEMARK OFFICE
CERTIFICATE OF CORRECTION

PATENT NO.        : 8,333,003 B2
APPLICATION NO.   : 12/123000
DATED             : December 18, 2012
INVENTOR(S)       : Mark Sagedahl et al.

It is certified that error appears in the above-identified patent and that said Letters Patent is hereby corrected as shown below:

In the Claims:

Column 12, Line 23:

Delete "stem" and insert -- stent --.

Signed and Sealed this
Fourth Day of June, 2013

Teresa Stanek Rea
*Acting Director of the United States Patent and Trademark Office*